US00PP27225P2

(12) United States Plant Patent
Horvath

(10) Patent No.: US PP27,225 P2
(45) Date of Patent: Oct. 4, 2016

(54) ***GEUM* PLANT NAMED 'DARK AND STORMY'**

(50) Latin Name: ***Geum* hybrid**
Varietal Denomination: Dark and Stormy

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 80 days.

(21) Appl. No.: 14/121,871

(22) Filed: Oct. 29, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg

(57) ABSTRACT

A new, distinct *Geum* plant as described and illustrated, characterized by ruffled semi double to single orange-red flowers of RHS N30 A that fade to N30 B and C.

1 Drawing Sheet

Latin name: *Geum* hybrid.
Cultivar name: 'Dark and Stormy'.

BACKGROUND OF THE INVENTION

The present invention relates to a new and distinct hybrid of *Geum* plant named 'Dark and Stormy' characterized by ruffled semi double to single orange-red flowers that fade to orange. The new *Geum* was the result of a breeding program in Hebron, Ill. since 2006. The new *Geum* was grown from seed collected on a group of open pollinated plants. The seed was sown in a greenhouse and the new plant was selected as a chance seedling. The selection of the new plant was made in 2010 and was due to its' ruffled semi double to single orange-red flowers that fade to orange. The initial asexual propagation of the new *Geum* plant was by division and took place at a nursery in Hebron, Ill. since 2011. Continued asexual propagation by division since that time has shown that the unique features of the new *Geum* plant are stable and reproduced true to type in successive generations.

SUMMARY OF THE INVENTION

In the following description, color references are made to The Royal Horticultural Society Colour Chart (2001). The new *Geum* plant named 'Dark and Stormy' characterized by ruffled semi double to single flowers of orange-red RHS N30 A fading to N30 B and C have been observed to be unique and stable.

Plants of the new, *Geum* can be compared to *Geum* 'Mai Tai' U.S. Pat. No. 22,433, patented. 1. The new plant flower color is orange-red RHS N30 A fading to N30 B and C while *Geum* 'Mai Tai' has a flower of RHS 53 B fading to 48 C and finally to 36 B and 36 C.

Plants of the new *Geum* can also be compared to *Geum* 'Sangria' not patented. 1. The new plant flower color is orange-red RHS N30 A while Geum 'Sangria' has a flower color of red RHS 45 B. 2. The new plant also has flowers that measure 3 cm wide while *Geum* 'Sangria' has flowers that measure 5-6 cm wide.

DESCRIPTION OF PHOTOGRAPHS

Figure 1:
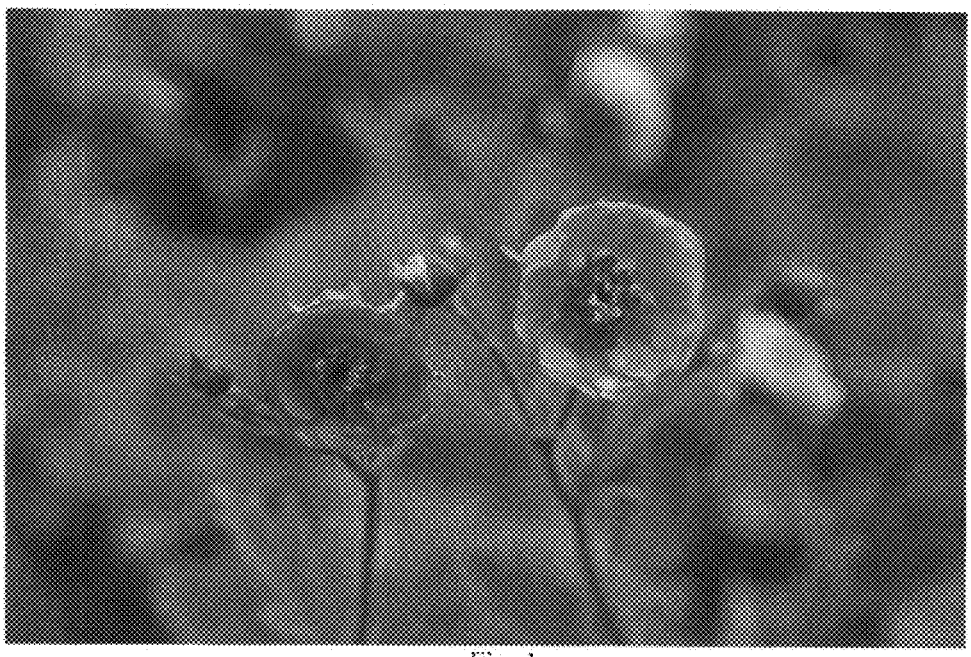

FIG. 1. Close up of the flower. Showing both the opening color and the fading color.

Figure 2:
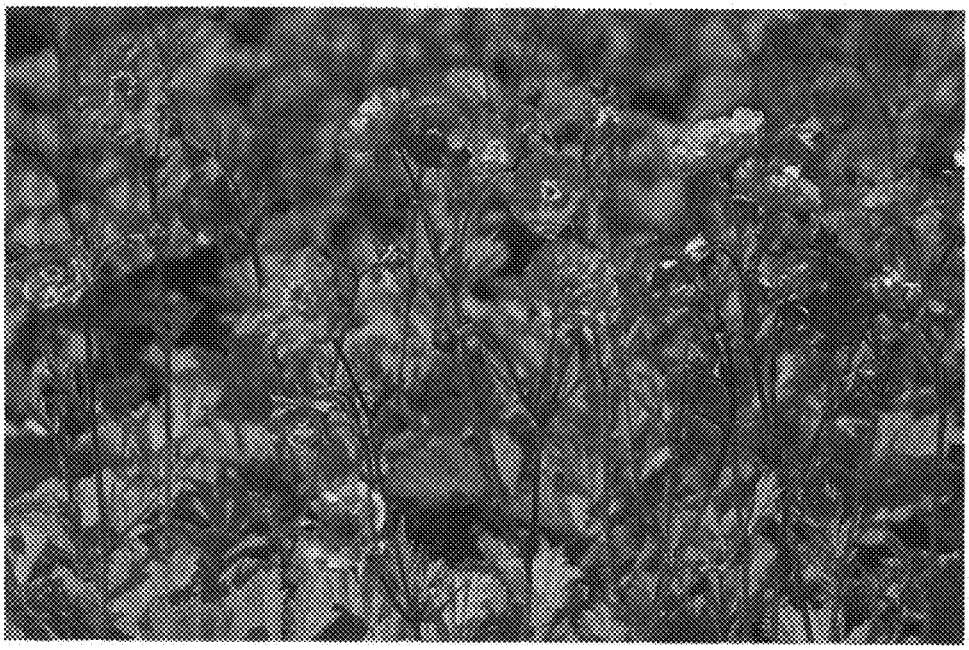

FIG. 2. Blooming plants in May.

DETAILED BOTANICAL DESCRIPTION

In the following description, color references are made to The Royal Horticultural Society Colour Chart (2001). Plants used for the description were grown in a 3 gallon container for 2 years at a nursery in Hebron, Ill. Measurements and numerical values represent averages of typical plants.

Botanical classification: *Geum* hybrid cultivar 'Dark and Stormy'.

Parentage: Unknown.

Propagation: Vegetative division.

Plant description: Overall habit of the new *Geum* is basal clumps, with upright green flower stems topped by ruffled semi double to single flowers of a orange-red color RHS N30 A fading to N30 B and C.

*Plant height.*—42 cm.

*Plant width.*—40 cm.

*Stem.*—Diameter: 3 mm.

*Stem or basal branches.*—Length up to 42 cm, with the internodes between basal foliage and first leaflet length being 2 cm and the second internodes between the first leaflet and the second leaflet length being 7 cm and the third internodes between the second and third leaflet length being 8 cm.

*Stem coloration.*—Of the whole stem is RHS 145 A.

Foliage description:

*Type.*—Herbaceous.

*Arrangement.*—Basal alternate with typically two or three lateral leaflets per stem.

*Petiole.*—Up to 12 cm long, with a diameter of 2 mm, color is 145 A.

*Terminal leaflet length.*—Typically 15 mm.

*Terminal leaflet width.*—Typically 5 mm.

*Terminal leaflet shape.*—Obovate with incised margins.

*Terminal and lateral leaf apex.*—Acute.

*Terminal and lateral leaf base.*—Cuneate.

*Terminal and lateral leaf margin.*—Incised.

*Texture.*—Terminal and lateral leaf, upper and lower surfaces: pubescent.

*Venation pattern.*—Terminal and lateral leaf, upper and lower surfaces: pinnate.

*Venation color*.—Terminal and lateral leaf, upper surface is color 137 A and lower surface color is 145 C.

*Lateral leaflet number*.—2 or 3 per stem.

*Lateral leaflet length*.—6 cm.

*Lateral leaflet width*.—Up to 2 cm.

*Lateral leaflet shape*.—Obovate.

*Adaxial leaf description*.—Color is 137 A.

*Abaxial leaf description*.—Color 146 B.

Flower description:

*Flower type*.—Corymb.

*Adaxial flower color*.—N30 A fading to N30 B and C.

*Abaxial flower color*.—35 A fading to close to 23 C and 24 B.

*Flower size*.—Diameter: 30 mm across, depth 10-15 mm.

*Flower number*.—5 per stem, 155-175 per plant.

*Number flowering stems*.—35.

*Bloom period and duration*.—Beginning the first week of May into the first week of June in Hebron, Ill.

*Flower longevity and duration on the plant*.—Approximately 3-4 weeks.

*Flower longevity and duration cut*.—Approximately 5-7 days.

*Scent*.—None.

*Petal count*.—12-18.

*Petal shape*.—Spathulate.

*Petal arrangement*.—Rotate, overlapping.

*Petal diameter or width*.—12 mm across and petal length — 10 mm long.

*Petal apex*.—Retuse, base: attenuate, margin: entire.

*Petal texture*.—Upper and lower surfaces: smooth, glabrous.

*Petal color*.—Upper surface is color N30 A fading to N30 B and C.

*Petal color*.—Lower surface color is close to 35 A fading to close to 23 C and 24 B.

*Petal venation*.—Type — reniform, vein color — upper surface close to N34 A, Lower surface close to N34 B.

*Inflorescence diameter and height*.—10 cm across, 10 cm long.

*Flower buds*.—Diameter: 11 mm across, depth: 10 mm, shape: ovoid, surface: slightly pubescent and color 59A.

*Sepal size*.—Length: up to 11 mm, diameter: 5 mm at base coming to a point.

*Sepal quantity*.—6.

*Sepal shape*.—Lanceolate, apex: acute, base: cuneate, margin: entire.

*Sepal texture*.—Upper and lower surfaces: Pubescent.

*Sepal color*.—Adaxial color 146 B. Abaxial color close to 146 A.

*Peduncle size and color*.—Length: 20 cm, diameter: 2 mm and color 145 A.

*Pedicel size and color*.—Length: 4-8 cm, diameter: 1-2 mm and color 145 B.

*Reproductive organs*.—Stamen — quantity over 100, length 1 cm. Anther — quantity: over 100, length: 1 mm, diameter: close to 0.5 mm. Pollen — typically present, color: 12A. Stigma — none observed. Style — number: over 50, length: 6 mm. Pistil — number: over 50, length: 6+ mm. Ovaries — none observed.

*Fruit*.—None observed.

*Hardiness*.—USDA zone 4-8.

Disease resistance: Resistance to diseases common to, *Geum* has not been observed on plants grown under nursery conditions.

I claim:

1. A new, distinct, *Geum* plant as described and illustrated, characterized by ruffled semi double to single orange-red flowers of RHS N30 A that fade to N30 B and C.

* * * * *